United States Patent [19]

Barney et al.

[11] Patent Number: 5,348,964
[45] Date of Patent: Sep. 20, 1994

[54] PIPERIDYL ETHERS AND THIOETHERS AS INHIBITORS OF CHOLESTEROL BIOSYNTHESIS

[75] Inventors: Charlotte L. Barney, Cincinnati; James R. McCarthy, West Chester; Marion W. Wannamaker, Cincinnati, all of Ohio

[73] Assignee: Merrell Dow Pharmaceuticals Inc., Cincinnati, Ohio

[21] Appl. No.: 92,278

[22] Filed: Jul. 15, 1993

Related U.S. Application Data

[63] Continuation of Ser. No. 919,993, Jul. 27, 1992, abandoned, which is a continuation of Ser. No. 851,454, Mar. 16, 1992, abandoned, which is a continuation of Ser. No. 557,877, Jul. 25, 1990, abandoned.

[51] Int. Cl.$^5$ .................. H01N 43/40; C07D 211/20
[52] U.S. Cl. .................... 514/315; 514/829; 546/242; 546/248
[58] Field of Search ............... 514/315, 829; 546/242, 546/248

[56] References Cited

U.S. PATENT DOCUMENTS

| | | | |
|---|---|---|---|
| 3,382,180 | 5/1968 | Priestley et al. | 252/152 |
| 3,871,863 | 3/1975 | Dorschner et al. | 71/88 |
| 4,244,963 | 1/1981 | Grier et al. | 546/258 |
| 4,316,903 | 2/1982 | Grier et al. | 546/208 |
| 4,758,564 | 7/1988 | Rentzea et al. | 546/258 |
| 5,084,461 | 1/1992 | Wannamaker et al. | 514/307 |

FOREIGN PATENT DOCUMENTS

| | | |
|---|---|---|
| 36086/89 | 6/1988 | Australia. |
| 0420116 | 4/1991 | European Pat. Off.. |
| 0468434 | 1/1992 | European Pat. Off.. |
| 0468457 | 1/1992 | European Pat. Off.. |

OTHER PUBLICATIONS

Danilov, et al., Chemical Abstracts 102(2) abstract #16497c, Jan. 14, 1985.
Gevaza, et al., Chemical Abstracts 90(21) abstract #168521c, May 21, 1979.
Mercer, et al., Comp. Biochem. Physiol., 80B(2): 341–346 (1985).
Gerst, et al., Biochemical Pharmacology 37(10): 1955–1964 (1988).

*Primary Examiner*—C. Warren Ivy
*Assistant Examiner*—Raymond Covington
*Attorney, Agent, or Firm*—Charlotte L. Barney

[57] ABSTRACT

The present invention relates to certain novel piperidyl ethers and thioethers which are useful as inhibitors of cholesterol biosynthesis and as agents which lower total serum cholesterol in patients in need thereof.

13 Claims, No Drawings

PIPERIDYL ETHERS AND THIOETHERS AS INHIBITORS OF CHOLESTEROL BIOSYNTHESIS

CROSS-REFERENCE TO RELATED APPLICATION

This is a continuation of application Ser. No. 07/919,993, filed Jul. 27, 1992, now abandoned, which was a continuation of application Ser. No. 07/851,454, filed Mar. 16, 1992, now abandoned; which was a continuation of application Ser. No. 07/557,877, filed Jul. 25, 1990, now abandoned.

BACKGROUND OF THE INVENTION

The present invention relates to certain novel piperidyl ethers and thioethers which are useful as inhibitors of cholesterol biosynthesis and as agents which lower total serum cholesterol in patients in need thereof. The present invention also provides pharmaceutical compositions for the use of these novel compounds.

The conversion of the acyclic polyolefin squalene to the cyclic steroid lanosterol is a key step in the biogenesis of cholesterol. This conversion occurs in two steps. Squalene epoxidase catalyzes the conversion of squalene to (3S)-2,3oxidosqualene. Oxidosqualene cyclase then converts (3S)-2,3-oxidosqualene to lanosterol. Lanosterol is converted through a number of subsequent enzymatic steps to cholesterol. Inhibition of squalene epoxidase decreases the amount of oxidosqualene available for conversion to cholesterol. Inhibition of oxidosqualene cyclase decreases the amount of lanosterol available for conversion to cholesterol. Inhibition of squalene epoxidase and/or oxidosqualene cyclase thus results in a decrease in the amount of cholesterol synthesized and ultimately causes a lowering of cholesterol in the blood.

Atherosclerosis as manifested in its major clinical complication, ischaemic heart disease, continues to be a major cause of death in industrialized countries. It is now well accepted that atherosclerosis can begin with local injury to the arterial endothelium followed by proliferation of arterial smooth muscle cells from the medial layer to the intimal layer along with deposition of lipid and accumulation of foam cells in the lesion. As the atherosclerotic plaque develops it progressively occludes more and more of the affected blood vessel and can eventually lead to ischaemia or infarction. Therefore, it is desirable to provide methods of inhibiting the progression of atherosclerosis in patients in need thereof.

There is now a large body of evidence demonstrating that hypercholesterolemia is an important risk factor associated with heart disease. For example, in December 1984, a National Institute of Health Consensus Development Conference Panel concluded that lowering definitely elevated blood cholesterol levels (specifically blood levels of low-density lipoprotein cholesterol) will reduce the risk of heart attacks due to coronary heart disease. Accordingly, it is desirable to provide a method for reducing blood cholesterol in patients with hypercholesterolemia.

Typically, cholesterol is carried in the blood of warm-blooded animals in certain lipid-protein complexes such as chylomicrons, very low density lipoprotein (VLDL), low density lipoprotein (LDL), and high density lipoprotein (HDL). It is widely accepted that LDL functions in a way that directly results in deposition of the LDL cholesterol in the blood-vessel wall and that HDL functions in a way that results in the HDL picking up cholesterol from the vessel wall and transporting it to the liver where it is metabolized [Brown and Goldstein, Ann. Rev. Biochem. 52, 223 (1983); Miller, Ann. Rev. Med. 31, 97 (1980)]. For example, in various epidemiologic studies the LDL cholesterol levels correlate well with the risk of coronary heart disease whereas the HDL cholesterol levels are inversely associated with coronary heart disease [Patton et al., Clin. Chem. 29, 1890 (1983)]. It is generally accepted by those skilled in the art that reduction of abnormally high LDL cholesterol levels is effective therapy not only in the treatment of hypercholesterolemia but also in the treatment of atherosclerosis.

The novel piperidyl ethers and thioethers of the present invention are inhibitors of squalene epoxidase and/or oxidosqualene cyclase. These compounds thus inhibit cholesterol biosynthesis and are useful in lowering blood cholesterol in patients in need thereof.

In addition, many fungi, including *Microsporum canis, Ctenomyces mentagrophytes, Trichophyton rubrum, Phialophora uerrucosa, Cryptococcus neoformans, Candida tropicalis, Candida albicans,* Mucor species, *Aspergillus fumigatus, Sporotrichum schenckii* and Saprolegnia species, are dependant on the biosynthesis of endogenous ergosterol for their growth and reproduction as described in "Chemical Activities of Fungi" by J. W. Foster (Academic Press Inc. 1949). Inhibition of ergosterol biosynthesis provides an antifungal effect in that it prevents the growth and reproduction of these fungi. The novel piperidyl ethers and thioethers of the present invention inhibit ergosterol biosynthesis and thus are useful as antifungal agents.

SUMMARY OF THE INVENTION

The present invention relates to novel piperidyl ethers and thioethers of formula (1)

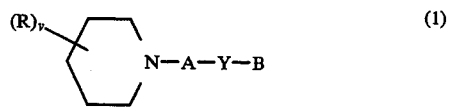

(1)

wherein
Y is oxygen, sulfur, sulfinyl or sulfonyl;
A is a $C_2$-$C_{15}$ alkylene having 0 to 5 double bonds;
B is a $C_2$-$C_{15}$ alkyl having 0 to 5 double bonds;
v is an integer 0, 1 or 2; and
R is hydroxy, $C_1$-$C_4$ alkyl or a radical of the formula (2)

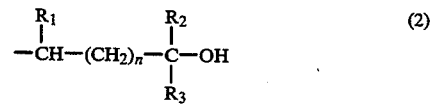

(2)

wherein
n is an integer 0, 1, 2 or 3; and
$R_1$, $R_2$ and $R_3$ are each independently hydrogen or a $C_1$-$C_4$ alkyl.

The present invention further provides a method of inhibiting the biosynthesis of cholesterol in a patient in need thereof comprising administering to said patient an effective cholesterol biosynthesis inhibiting amount of a compound of formula (1).

The present invention also provides a method of lowering plasma cholesterol in a patient in need thereof, and a method of treating a patient afflicted with hypercholesterolemia, comprising administering to said patient an effective hypocholesterolemic amount of a compound of claim 1.

DETAILED DESCRIPTION OF THE INVENTION

As used herein the term "Y" refers to an oxygen atom, a sulfur atom, a sulfinyl group or a sulfonyl group. In other words, the term "Y" refers to a divalent radical of the formula —O—, —S—, —S(O)— or —SO$_2$—. The term "halogen", or "halo" or "X" refers to a chlorine, bromine, or iodine atom.

As used herein the term "A" refers to a $C_2$-$C_{15}$ alkylene having 0 to 5 double bonds. The term "A" thus refers to a saturated or unsaturated hydrocarbylene radical of from 2 to 15 carbon atoms of straight or branched chain configuration. Specifically included within the scope of the term are the radicals —CH$_2$CH$_2$—, —CH$_2$CH$_2$CH$_2$—, —CH$_2$(CH$_2$)$_2$CH$_2$—, —CH$_2$(CH$_2$)$_3$CH$_2$—, —CH$_2$(CH$_2$)$_4$CH$_2$—, —CH$_2$(CH$_2$)$_5$CH$_2$—, —CH$_2$(CH$_2$)$_6$CH$_2$—, —CH$_2$(CH$_2$)$_7$CH$_2$—, —CH$_2$(CH$_2$)$_8$CH$_2$—, —CH$_2$(CH$_2$)$_9$CH$_2$—, —CH$_2$(CH$_2$)$_{10}$CH$_2$—, —CH$_2$(CH$_2$)$_{11}$CH$_2$—, —CH$_2$(CH$_2$)$_{12}$CH$_2$—, —CH$_2$(CH$_2$)$_{13}$CH$_2$—, —CH(CH$_3$)CH$_2$—, —CH(CH$_3$)CH$_2$CH$_2$—, —CH(CH$_3$)CH$_2$CH$_2$CH$_2$—, —CH(CH$_3$)CH$_2$(CH$_2$)$_2$CH$_2$—, —CH(CH$_3$)CH$_2$CH(CH$_3$)—, —CH(CH$_3$)CH$_2$CH$_2$CH(CH$_3$)—, —CH(CH$_3$)CH$_2$(CH$_2$)$_2$CH(CH$_3$)—, —C(CH$_3$)═CH—(CH$_2$)$_2$—C(CH$_3$)═CH—(CH$_2$)$_2$—C(CH$_3$)═CH—(CH$_2$)$_2$—C(CH$_3$)═CH—(CH$_2$)—, —CH(CH$_3$)—(CH$_2$)$_3$—CH(CH$_3$)—(CH$_2$)$_3$—CH(CH$_3$)—(CH$_2$)$_3$—CH(CH$_3$)—(CH$_2$)$_2$—.

As used herein the term "B" refers to a $C_2$-$C_{15}$ alkyl having 0 to 5 double bonds. The term "B" thus refers to a saturated or unsaturated hydrocarbyl radical of from 2 to 15 carbon atoms of straight or branched chain configuration. Specifically included within the scope of the term are the radicals —CH$_2$CH$_3$, —CH$_2$CH$_2$CH$_3$, —CH$_2$(CH$_2$)$_2$CH$_3$, —CH$_2$(CH$_2$)$_3$CH$_3$, —CH$_2$(CH$_2$)$_4$CH$_3$, —CH$_2$(CH$_2$)$_5$CH$_3$, —CH$_2$(CH$_2$)$_6$CH$_3$, —CH$_2$(CH$_2$)$_7$CH$_3$, —CH$_2$(CH$_2$)$_8$CH$_3$, —CH$_2$(CH$_2$)$_9$CH$_3$, —CH$_2$(CH$_2$)$_{10}$CH$_3$, —CH$_2$(CH$_2$)$_{11}$CH$_3$, —CH$_2$(CH$_2$)$_{12}$CH$_3$, —CH$_2$(CH$_2$)$_{13}$CH$_3$, —CH(CH$_3$)CH$_2$CH$_3$, —CH(CH$_3$)CH$_2$CH$_2$CH$_3$, —CH(CH$_3$)CH$_2$(CH$_2$)$_2$CH$_3$, —CH(CH$_3$)CH$_3$, —CH(CH$_3$)CH$_2$CH$_2$CH$_3$, —CH(CH$_3$)CH$_2$(CH$_2$)$_2$CH$_2$CH$_3$, —C(CH$_3$)═CH—(CH$_2$)$_2$—C(CH$_3$)═CH—(CH$_2$)$_2$—C(CH$_3$)═CH—(CH$_2$)$_2$—C(CH$_3$)═CH—CH$_3$, —CH(CH$_3$)—(CH$_2$)$_3$—CH(CH$_3$)—(CH$_2$)$_3$—CH(CH$_3$)—(CH$_2$)$_3$—CH(CH$_3$)—(CH$_2$)—CH$_3$.

The compounds of formula (1) bear a piperidyl moiety which can be unsubstituted or substituted with one or two substituents selected from the group consisting of hydroxy, $C_1$-$C_4$ alkyl or a radical of the formula —CH(R$_1$)—(CH$_2$)$_n$—C(R$_2$)(R$_3$)OH, wherein n is an integer 0, 1, 2 or 3; and R$_1$, R$_2$ and R$_3$ are each independently hydrogen or a $C_1$-$C_4$ alkyl. As used herein the term "$C_1$-$C_4$ alkyl" refers to a saturated hydrocarbyl radical of from 1 to 4 carbon atoms of straight or branched chain configuration, including methyl, ethyl, n-propyl, isopropyl, n-butyl, isobutyl and t-butyl. The piperidyl moiety may bear substituents in any of the 2, 3, 4, 5 or 6 positions. In those instances wherein the piperidyl ring of the compound of formula (1) bears two substituents, the two substituents may be attached at the same or at different carbon atoms in the piperidyl ring. More particularly, the following piperidyl moieties are specifically contemplated as being included within the scope of formula (1):

1-piperidyl, 4-hydroxypiperidyl, 4-hydroxy-3,3-dimethyl piperidyl, 3-hydroxypiperidyl, 3,4-dihydroxypiperidyl, 2-methylpiperidyl, 3-methylpiperidyl, 4-methylpiperidyl, 3,4-dimethylpiperidyl, 2,4-dimethylpiperidyl, 2,3-dimethylpiperidyl, 2,2-dimethylpiperidyl, 3,3-dimethylpiperidyl, 4,4-dimethylpiperidyl, 2-[(3-hydroxy)-4-piperidinyl]propanol, 2-[(2-methyl)-4-piperidinyl]propanol, 2-[(3-methyl)-4-piperidinyl]propanol.

The compounds of formula (1) wherein Y is sulfur or oxygen and R is hydroxy or $C_1$-$C_4$ alkyl can be prepared by utilizing procedures and techniques well known and appreciated by one of ordinary skill in the art. A general synthetic scheme for preparing these compounds is set forth in Scheme A wherein all substituents, unless otherwise indicated, are previously defined.

Scheme A

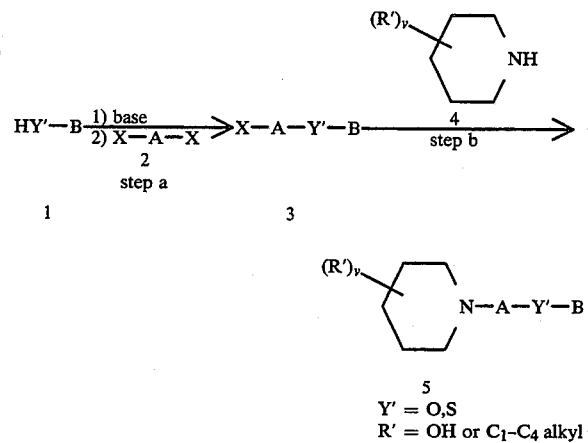

Scheme A provides a general synthetic scheme for preparing compounds of formula (1) wherein Y is oxygen or sulfur and R is hydroxy or $C_1$-$C_4$ alkyl. In general, an N-alkylated piperidine compound of structure 5 can be prepared in two steps.

In step a, an appropriate haloalkylene alkylsulfide compound or haloalkylene alkylether compound of structure 3 can be prepared by a Williamson type reaction. For example, an appropriate thiol compound or alcohol compound of structure 1 can first be converted to its sodium salt. For example, a thiol compound of structure 1 can be converted to the corresponding sodium salt by reaction with sodium ethoxide in a suitable solvent, such as absolute ethanol. An alcohol compound of structure 1 can be converted to the corresponding sodium salt by reaction with sodium metal in a suitable solvent, such as excess alcohol compound of structure 1. The appropriate sodium thioalkoxide compound or sodium alkoxide compound is then reacted with the appropriate bis-haloalkylene compound of structure Z in a suitable protic solvent, as described above, to give the appropriate haloalkylene alkylsulfide compound or haloalkylene alkylether compound of structure 3.

In step b, the appropriate N-alkylated piperidine compound of structure 5 can be prepared by reacting the appropriate piperidine compound of structure 4 with the appropriate haloalkylene alkylsulfide compound or haloalkylene alkylether compound of structure 3 in the presence of a base, such as excess piperidine compound 4 or pyridine.

Starting materials for use in the general synthetic procedures outlined in Scheme A are readily available to one of ordinary skill in the art. For example, 4-hydroxy-3,3-dimethyl-N-methylpiperidine is described in *Isv. Akad. Nauk* SSSR, Ser, Khim., (1), 2575–82(1968). The 4-hydroxy-3,3-dimethylpiperidine can be obtained by N-demethylation of the 4-hydroxy-3,3-dimethyl-N-methylpiperidine by techniques and procedures well known in the art such as described in *Tetrahedron Letters*, 5049(1970).

The following examples present typical syntheses as described in Scheme A. These examples are understood to be illustrative only and are not intended to limit the scope of the present invention in any way. As used herein, the following terms have the indicated meanings: "g" refers to grams; "mg" refers to milligrams; "mmol" refers to millimoles; "mL" refers to milliliters; "bp" refers to boiling point; "° C." refers to degrees Celsius; "mm Hg" refers to millimeters of mercury; "μL" refers to microliters; "μg" refers to micrograms; and "μM" refers to micromolar.

EXAMPLE 1

5-(1-Piperidyl)pentyl isopentyl sulfide, hydrochloride salt

Step a:

Generate sodium ethoxide by carefully adding sodium metal (620 mg, 27 mmol) to absolute ethanol (25 mL) under nitrogen atmosphere and stirring until evolution of hydrogen gas ceases. Cool to 0° C. and add, by dropwise addition, a solution of 3-methyl-1-butanethiol (2.8 g, 27 mmol) in absolute ethanol (25 mL). Stir for 30 mintutes at 0° C., cool to −70° C. and transfer via cannula to another flask containing a solution of 1-bromo-5-chloropentane (5.0 g, 27 mmol) in absolute ethanol (25 mL) at −30° C. Stir at −30° C. for 30 minutes, then allow to warm to room temperature and stir overnight. Add additional sodium ethoxide and stir for 30 minutes at room temperature. Concentrate in vacuo, partition between water and ethyl ether and separate the organic phase. Extract the aqueous phase with ethyl ether (2×50 mL), combine the organic phases and dry (MgSO$_4$). Evaporate the solvent in vacuo to yield 4.89 g of 5-chloropentyl isopentyl sulfide as a clear oil; MS (CI/CH$_4$) m/z 209(M+1), 173(M+1-HCl).

Step b:

Mix 5-chloropentyl isopentyl sulfide (1.0 g, 4.79 mmol) and piperidine (3 mL, 28.7 mmol) and heat at 125° C. overnight. Cool to room temperature and partition between 50% sodium hydroxide and ethyl ether. Separate the organic phase and extract the aqueous phase with ethyl ether (2×30 mL). Combine the organic phases and dry (MgSO$_4$). Evaporate the solvent in vacuo to yield 810 mg yellow oil. Dissolve the oil in ethyl ether (100 mL) and treat with anhydrous hydrochloric acid. Collect the pink solid by vacuum filtration and recrystallize (ethyl acetate) to yield 200 mg of the title compound as white crystals; mp 155°–156° C. 242E-76

Anal. Calcd for C$_{15}$H$_{31}$NS.HCl: C, 61.29; H, 10.97; N, 4.76; Found: C, 61.26; H, 11.10; N, 4.70

EXAMPLE 2

9-(1-Piperidyl)nonanyl isopropyl ether

Step a:

Generate sodium isopropoxide by carefully adding sodium metal (161 mg, 6.99 mmol) to isopropanol (10 mL) and stirring until evolution of hydrogen gas ceases. Add 1,9dibromononane (2.0 g, 6.99 mmol) and stir for 9 days at room temperature. Add water (50 mL) and remove the volatiles in vacuo. Partition the residue between saturated sodium chloride and ethyl acetate. Separate the organic phase and extract the aqueous phase with ethyl acetate (2×50 mL). Combine the organic phases and dry (MgSO$_4$). Evaporate the solvent in vacuo to yield 1.91 g pale yellow oil. Purify by silica gel chromatography (hexane then ethyl acetate) to yield 730 mg of 9-bromononanyl isopropyl ether as a yellow oil; MS (CI/CH$_4$) m/z 265(M+1).

Step b:

Mix 9-bromononanyl isopropyl ether (730 mg, 2.75 mmol) and piperidine (1 mL, 10 mmol) and stir at room temperature overnight. Add additional piperidine (5 mL) and heat at 100° C. for 4 hours. Partition between ethyl ether and 5N sodium hydroxide. Separate the organic phase and extract the aqueous phase with ethyl ether (2×30 mL). Combine the organic phases and dry (MgSO$_4$). Evaporate the solvent in vacuo to yield 510 mg yellow oil. Purify by silica gel chromatography (ethyl acetate followed by 10% MeOH/ethyl acetate) to yield 380 mg (51%) of the title compound as a pale yellow oil.

Anal. Calcd for C$_{17}$H$_{35}$NO: C, 75.77; H, 13.09; N, 5.20; Found: C, 75.36; H, 13.04; N, 5.02.

EXAMPLE 3

3-(1-Piperidyl)propyl isopentyl sulfide, hydrochloride salt

Step a:

Mix 1-bromo-3-chloropropane (5.0 g, 31.76 mmol), absolute ethanol (25 mL), and 3-methyl-1-butanethiol (3.3 g, 31.76 mmol). Place under nitrogen atmosphere and cool to 0° C. In a separate flask, generate sodium ethoxide by carefully adding sodium metal (736 mg, 32 mmol) to absolute ethanol (25 mL) and stirring under nitrogen atmosphere until evolution of nitrogen gas ceases. Add the sodium ethoxide, by dropwise addition, to the above mixture and stir at room temperature for 72 hours. Partition between water and ethyl ether and separate the organic phase. Extract the aqueous phase with ethyl ether (2×50 mL), combine the organic phases and dry (MgSO$_4$). Evaporate in vacuo to yield 3.0 g (52%)3-chloropropyl isopentyl sulfide as a clear oil; MS (CI/CH$_4$) m/z 181(M+1).

Step b:

Mix 3-chloropropyl isopentyl sulfide (1.0 g, 5.5 mmol) and piperidine (3.3 mL, 33 mmol) and heat at 125° C. for 2 hours. Cool to room temperature and partition between 50% sodium hydroxide and ethyl ether. Separate the organic phase, wash the aqueous phase with ethyl ether (2×30 mL), combine the organic phases and dry (MgSO$_4$). Evaporate the solvent in vacuo to yield 1.12 g (89%). Dissolve the product (1.0 g) in ethyl ether (100 mL) and treat with anhydrous hydrochloric acid. Collect the resulting yellow solid by vacuum filtration, recrystallize (ethyl acetate) and dry to yield 0.723 g of the title compound as white crystals; mp 155°–8° C. 438E-83

Anal. Calcd for $C_{13}H_{27}NS \cdot HCl$: C, 58.73; H, 10.61; N, 5.27; Found: C, 58.49; H, 10.98; N, 5.31.

EXAMPLE 4

2-(1-piperidyl)ethyl ethyl sulfide, hydrochloride salt

Step b:

Heat 2-chloroethyl ethylsulfide (0.934 g, 7.5 mmol) and piperidine (4.5 mL, 45 mmol) at 125° C. for 3 hours. Cool to room temperature, partition between 50% sodium hydroxide and ethyl ether and separate the organic phase. Wash the aqueous phase with ethyl ether (2×25 mL), combine the organic phases and dry (MgSO4). Evaporate the solvent in vacuo to yield 1.34 g (99%) yellow oil. Dissolve the oil in ethyl ether and treat with anhydrous hydrochloric acid. Collect the resulting white solid by vacuum filtration and recrystallize (isopropanol/ethyl acetate) to yield 833 mg of the title compound as white crystals; mp 194°–196° C.

Anal. Calcd for $C_9H_{19}NS \cdot HCl$: C, 51.53; H, 9.61; N, 6.68; Found: C, 51.43; H, 9.76; N, 6.58.

EXAMPLE 5

5-[1-(4-Hydroxy)piperidyl]pentyl isopentyl sulfide

Step b:

Mix 5-chloropentyl isopentyl sulfide (1.0 g, 4.79 mmol) and 4-hydroxypiperidine (3 g, 28.7 mmol) and heat at 125° C. overnight. Cool to room temperature and partition between 50% sodium hydroxide and ethyl ether. Separate the organic phase and extract the aqueous phase with ethyl ether (2×30 mL). Combine the organic phases and dry (MgSO4). Evaporate the solvent in vacuo and purify by silica gel chromatography to give the title compound.

The following compounds can be prepared by procedures analogous to those described above in Examples 1–5:

5-[1-(3-hydroxy)piperidyl]pentyl isopentyl sulfide
5-[1-(3,4-dihydroxy)piperidyl]pentyl isopentyl sulfide
3-[1-(3-hydroxy)piperidyl]propyl isopentyl sulfide
3-[1-(3,4-dihydroxy)piperidyl]propyl isopentyl sulfide
4-(1-piperidyl)butyl ethyl sulfide
2-(1-piperidyl)ethyl butyl sulfide
2-(1-piperidyl)ethyl pentyl sulfide
2-(1-piperidyl)ethyl hexyl sulfide
4-[1-(4-methyl)piperidyl]butyl ethyl sulfide
2-[1-(3-methyl)piperidyl]ethyl butyl sulfide
2-[1-(3,4-dimethyl)piperidyl]ethyl pentyl sulfide
9-(1-piperidyl)nonanyl isopropyl ether
9-[1-(4-hydroxy)piperidyl]nonanyl isopropyl ether
9-[1-(3,4-dihydroxy)piperidyl]nonanyl isopropyl ether
9-[1-(3-hydroxy)piperidyl]nonanyl isopropyl ether
3-(1-piperidyl)propyl isopropyl ether
4-(1-piperidyl)butyl isopropyl ether
5-[1- (4-hydroxy-3,3-dimethyl)piperidyl]pentyl isopentyl sulfide
5-[1-(4-hydroxy-3,3-dimethyl)piperidyl]pentyl isopentyl ether.

The compounds of formula (1) wherein Y is sulfinyl or sulfonyl and R is hydroxy or $C_1$–$C_4$ alkyl can be prepared by utilizing procedures and techniques well known and appreciated by one of ordinary skill in the art. A general synthetic scheme for preparing these compounds is set forth in Scheme B wherein all substituents, unless otherwise indicated, are previously defined.

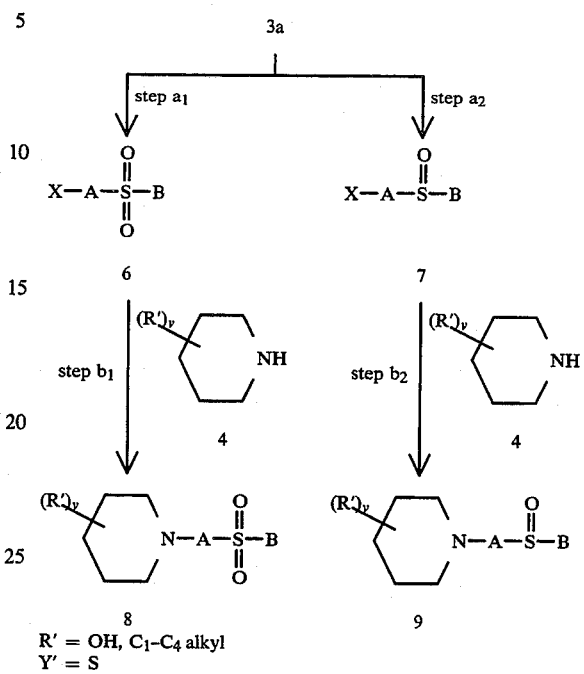

Scheme B

R' = OH, $C_1$–$C_4$ alkyl
Y' = S

Scheme B provides a general synthetic scheme for preparing compounds of formula (1) wherein Y is sulfinyl or sulfonyl and R is hydroxy or $C_1$–$C_4$ alkyl. In general, N-alkylated piperidine compounds of structures 8 and 9 can be prepared from an appropriate haloalkylene alkyl sulfide compound of structure 3a (described previously in Scheme A, Y'=S) in a two-step process.

In step $a_1$, the appropriate haloalkylene alkyl sulfide compound of structure 3a can be oxidized to the corresponding sulfone compound of structure 6 by techniques and procedures well known and appreciated in the art. For example, an appropriate haloalkylene alkyl sulfone compound of structure 6 can be prepared by reacting the appropriate haloalkylene alkyl sulfide compound of structure 3a with two equivalents of meta-chloroperbenzoic acid in a suitable aprotic solvent, such as methylene chloride.

Similarly, in step $a_2$, the appropriate haloalkylene alkyl sulfide compound of structure 3a can be oxidized to the corresponding sulfoxide compound of structure 7. For example, an appropriate haloalkylene alkyl sulfoxide compound of structure 7 can be prepared by reacting the appropriate haloalkylene alkyl sulfide compound of structure 3a with one equivalent of meta-chloroperbenzoic as described above in step $a_1$.

In step $b_1$, the appropriate N-alkylated piperidine compound of structure 8 can be prepared by reacting the appropriate piperidine compound of structure 4 with the appropriate haloalkylene alkylsulfone compound of structure 6 in the presence of a base, such as excess piperidine compound 4 or pyridine.

Similarly, in step $b_2$, the appropriate N-alkylated piperidine compound of structure 9 can be prepared by reacting the appropriate piperidine compound of structure 4 with the appropriate haloalkylene alkyl sulfoxide compound of structure 7 as described above in step $b_1$.

Starting materials for use in the general synthetic procedures outlined in Schemes A and B are readily available to one of ordinary skill in the art.

The following examples present typical syntheses as described in Scheme B. These examples are understood to illustrative only and are not intended to limit the scope of the present invention in any way.

EXAMPLE 6

5-(1-piperidyl)pentyl isopentyl sulfoxide

Step a:

Dissolve 5-chloropentyl isopentyl sulfide (1.0 g, 5.39 mmol) in methylene chloride (25 mL), place under nitrogen atmosphere and cool to −20° C. Add, by dropwise addition, a solution of meta-chloroperbenzoic acid (930 mg, 5.39 mmol) in methylene chloride (25 mL). Stir overnight at room temperature. Add additional meta-chloroperbenzoic acid (930 mg). Stir briefly and filter. Treat with aqueous sodium metabisulfite (until negative starch-iodide test) and separate the layers. Wash the organic phase with saturated sodium hydrogen carbonate until basic and dry (MgSO$_4$). Evaporate the solvent in vacuo to yield a yellow oil. Purify by silica gel chromatography (50% ethyl acetate/hexane) to yield 750 mg of 5-chloropentyl isopentyl sulfoxide as a clear oil; MS (CI/CH$_4$) m/z 225(M+1), 189 (M+1-HCl).

Step b:

Heat 5-chloropentyl isopentyl sulfoxide (760 mg, 3.38 mmoL) and piperidine (2 mL) at 125° C. for 1 hour. Partition between 5N sodium hydroxide and ethyl ether. Separate the organic phase and extract the aqueous phase with ethyl ether (2×25 mL). Combine the organic phases and dry (MgSO$_4$). Evaporate the solvent in vacuo to yield 1.01 g yellow oil. Purify by silica gel chromatography (CHCl$_3$:MeOH:NH$_4$OH/100:10:1) to yield 740 mg (80%) yellow oil which crystallizes. Purify further by silica gel chromatography (50% methanol/methylene chloride) to yield 79 mg of the title compound as a white solid; mp 44°–45° C.

Anal. Calcd for C$_{15}$H$_{31}$NOS: C, 65.88; H, 11.45; N, 5.12; Found: C, 65.66; H, 11.80; N, 4.93.

EXAMPLE 7

5-(1-Piperidyl)pentyl isopentyl sulfone

Step a:

Dissolve 5-chloropentyl isopentyl sulfide (1.0 g, 5.39 mmol) in methylene chloride (25 mL), place under nitrogen atmosphere and cool to −20° C. Add, by dropwise addition, a solution of meta-chloroperbenzoic acid (930 mg, 5.39 mmol) in methylene chloride (25 mL). Stir for 72 hours at room temperature. Add additional meta-chloroperbenzoic acid (3 g). Stir for 1 hour. Treat with aqueous sodium metabisulfite (until negative starch-iodide test) and separate the layers. Wash the organic phase with saturated sodium hydrogen carbonate until basic and dry (MgSO$_4$). Evaporate the solvent in vacuo to yield 940 mg (72%) yellow oil. Purify by silica gel chromatography (50%ethyl acetate/hexane) to yield 770 mg (59.3%) of 5-chloropentyl isopentyl sulfone; MS (CI/CH$_4$) m/z 241(M+1), 205(M+1-HCl).

Step b:

Heat 5-chloropentyl isopentyl sulfone (770 mg, 3.2 mmoL) and piperidine (2 mL) at 125° C. for 1 hour. Partition between 5N sodium hydroxide and ethyl ether. Separate the organic phase and extract the aqueous phase with ethyl ether (2×25 mL). Combine the organic phases and dry (MgSO$_4$). Evaporate the solvent in vacuo to yield 590 mg orange oil. Purify by silica gel chromatography (CHCl$_3$:MeOH:NH$_4$OH/100:10:1) to yield 740 mg (80%) yellow oil which crystallizes. Purify further by silica gel chromatography (ethyl acetate) to yield 540 mg dark yellow oil. Purify further by silica gel chromatography (50% methanol/methylene chloride) to yield 80 mg of the title compound as a yellow oil.

Anal. Calcd for C$_{15}$H$_{31}$NO$_2$S: C, 62.24; H, 10.79; N, 4.84; Found: C, 62.17; H, 11.15; N, 4.70.

EXAMPLE 8

3-(1-Piperidyl)propyl isopentyl sulfoxide

Step a:

Dissolve 3-chloropropyl isopentyl sulfide (800 mg, 4.43 mmol) in methylene chloride (25 mL), cool to −20° C. and place under nitrogen atmosphere. Add a solution of metachloroperbenzoic acid (764 mg, 4.43 mmol) in methylene chloride (25 mL). Stir at −20° C. for 2 hours, then allow to warm to room temperature overnight. Treat with aqueous sodium metabisulfite (until negative starch-iodide test) and separate the layers. Wash the organic phase with saturated sodium hydrogen carbonate until basic and dry (MgSO$_4$). Evaporate the solvent in vacuo to yield 1.56 g yellow oil. Purify by silica gel chromatography (ethyl acetate) to yield 420 mg (48%) of 3-chloropropyl isopentyl sulfoxide as a pale yellow oil; MS (CI/CH$_4$) m/z 197(M+1), 161(M+1-HCl).

Step b:

Heat 3-chloropropyl isopentyl sulfoxide (400 mg, 2.03 mmol) and piperidine (1.0 g, 12 mmol) at 125° C. for 45 minutes. Cool to room temperature, treat with 5N sodium hydroxide, extract with ethyl acetate (3×25 mL), and dry (MgSO$_4$). Concentrate in vacuo to yield 240 mg yellow oil. Purify by silica gel chromatography (50% ethyl acetate/methanol) to yield 180 mg of the title compound as a clear oil.

Anal. Calcd for C$_{13}$H$_{27}$NOS: C, 63.61; H, 11.09; N, 5.71; Found: C, 63.23; H, 11.02; N, 5.32.

EXAMPLE 9

3-(1-Piperidyl)propyl isopentyl sulfone

Step a:

Dissolve 3-chloropropyl isopentyl sulfide (800 mg, 4.43 mmol) in methylene chloride (25 mL) and place under nitrogen atmosphere. Add a solution of meta-chloroperbenzoic acid (1.53 g, 8.85 mmol) in methylene chloride (25 mL). Stir at room temperature overnight. Add additional meta-chloroperbenzoic acid (1.0 g) in methylene chloride (25 mL). Stir at room temperature overnight. Treat with aqueous sodium metabisulfite (until negative starch-iodide test) and separate the layers. Wash the organic phase with saturated sodium hydrogen carbonate until basic and dry (MgSO$_4$). Evaporate the solvent in vacuo to yield 710 mg (75.4%) of 3-chloropropyl isopentyl sulfone as a yellow oil which crystallizes; MS (CI/CH$_4$) m/z 213(M+1), 177(M+1-HCl).

Step b:

Heat 3-chloropropyl isopentyl sulfone (700 mg, 3.29 mmol) and piperidine (1.7 g, 20 mmol) at 125° C. for 45 minutes. Cool to room temperature, treat with 5N sodium hydroxide, extract with ethyl acetate (3×25 mL), and dry (MgSO$_4$). Concentrate in vacuo to yield 850 mg orange oil. Purify by silica gel chromatography (50% ethyl acetate/methanol) to yield 500 mg of the title compound as a pale yellow oil.

Anal. Calcd for $C_{13}H_{27}NO_2S$: C, 59.73; H, 10.41; N, 5.36; Found: C, 59.62; H, 10.44; N, 4.96.

EXAMPLE 10

2-(1-Piperidyl)ethyl ethyl sulfoxide

Step a:

Dissolve 2-chloroethyl ethyl sulfide (1.0 g, 8.02 mmol) in methylene chloride (25 mL), cool to -20° C. and place under nitrogen atmosphere. Add a solution of metachloroperbenzoic acid (1.4 g, 8.02 mmol) in methylene chloride (25 mL). Stir at −20° C. for 4 hours, then allow to stir at room temperature overnight. Add additional meta-chloroperbenzoic acid (0.5 g) and stir for 1 hour at room temperature. Treat with aqueous sodium metabisulfite (until negative starch-iodide test) and separate the layers. Wash the organic phase with saturated sodium hydrogen carbonate until basic and dry ($MgSO_4$). Evaporate the solvent in vacuo to yield 1.0 g of 2-chloroethyl ethyl sulfoxide as a clear oil; MS ($CI/CH_4$) m/z 141(M+1).

Step b:

Heat 2-chloroethyl ethyl sulfoxide (1.0 g, 7.1 mmol) and piperidine (2 mL, 20 mmol) at 60° C. for 2 hours. Treat with 5N sodium hydroxide, extract with ethyl acetate (3×50 mL) and dry ($MgSO_4$). Concentrate in vacuo to yield 800 mg orange oil. Purify by silica gel chromatography (50% ethyl acetate/methanol) to yield 560 mg (42%) of the title compound as a yellow oil. 438E-25 MDL 101135

Anal. Calcd for $C_9H_{19}NOS$: C, 57.10; H, 10.12; N, 7.40; Found: C, 56.98; H, 9.98; N, 7.02.

EXAMPLE 11

2-(1-Piperidyl)ethyl ethyl sulfone

Step a:

Dissolve 2-chloroethyl ethyl sulfide (1.0 g, 8.02 mmol) in methylene chloride (25 mL) and place under nitrogen atmosphere. Add a solution of metachloroperbenzoic acid (2.8 g, 16.04 mmol) in methylene chloride (25 mL). Stir at room temperature overnight. Add additional meta-chloroperbenzoic acid (1.5 g) and stir for 1 hour at room temperature. Treat with aqueous sodium metabisulfite (until negative starch-iodide test) and separate the layers. Wash the organic phase with saturated sodium hydrogen carbonate until basic and dry ($MgSO_4$). Evaporate the solvent in vacuo to yield 1.2 g of 2chloroethyl ethyl sulfone as a clear oil; MS ($CI/CH_4$) m/z 157(M+1).

Step b:

Mix 2-chloroethyl ethyl sulfone (1.2 g, 7.66 mmol) and piperidine (2 mL, 20 mmol). Stir at room temperature for 2 hours. Treat with 5N sodium hydroxide, extract with ethyl acetate (3×50 mL) and dry ($MgSO_4$). Concentrate in vacuo to yield 1.3 g yellow oil which crystallizes. Purify by silica gel chromatography (ethyl acetate) to yield 550 mg (35%) of the title compound as a clear oil which crystallizes; mp 45°–47° C.

Anal. Calcd for $C_9H_{19}NO_2S$: C, 52.65; H, 9.33; N, 6.82; Found: C, 53.12; H, 9.36; N, 6.50.

EXAMPLE 12

2-(1-Piperidyl)ethyl heptyl

Step a (Scheme A):

Mix 1-bromo-2-chloroethane (10.0 g, 69.2 mmol), absolute ethanol (50 mL), and heptanethiol (9.2 g, 69.2 mmol), place under nitrogen atmosphere and cool to 0° C. In a separate flask, generate sodium ethoxide by carefully adding sodium metal (1.61 g, 70 mmol) to absolute ethanol (50 mL) and stirring until evolution of hydrogen gas ceases. Add the sodium ethoxide, by dropwise addition, to the flask containing the above reagents and stir overnight. Partition between water and ethyl ether and separate the organic phase. Extract the aqueous phase with ethyl ether (2×50 mL), combine the organic phases and dry ($MgSO_4$). Evaporate the solvent in vacuo to yield 10.72 g clear oil. Purify by silica gel chromatography (hexane) to yield 3.9 g clear oil (86% pure) and 3.4 g (57% pure) of 2-chloroethyl heptyl sulfide:; MS ($CI/CH_4$) m/z 195(M+1), 159(M+1-HCl).

Step a (Scheme B):

Dissolve 2-chloroethyl heptyl sulfide (1.0 g, 5.13 mmol) in methylene chloride (50 mL), cool to −20° C. and place under nitrogen atmosphere. Add, by dropwise addition, a solution of meta-chlorperbenzoic acid (1.25 g, 6.0 mmol) in methylene chloride. Stir at −20° C. for 3 hours, then allow to warm to room temperature. Treat with saturated sodium meta bisulfite (until negative starch-iodide test) and basify with saturated sodium hydrogen carbonate. Extract with methylene chloride (2×25 mL), dry ($MgSO_4$) and evaporate in vacuo to yield 1.2 g of 2chloroethyl heptyl sulfoxide as white crystals; MS ($CI/CH_4$) m/z 211(M+1).

Step b:

Mix 2-chloroethyl heptyl sulfoxide (1.05 g, 5 mmol) and piperidine (10 mL). Stir at 60° C. overnight. Cool to room temperature, partition between 5N sodium hydroxide and ethyl ether. Separate the organic phase and extract the aqueous phase with ethyl ether (2×25 mL). Combine the organic phases, dry ($MgSO_4$) and evaporate in vacuo to yield 900 mg orange oil which crystallizes. Purify by silica gel chromatography (ethyl acetate) to yield 800 mg of the title compound as a yellow oil which crystallizes; mp 35°–36° C., MS ($CI/CH_4$) m/z 260(M+1).

EXAMPLE 13

2-(1-Piperidyl)ethyl heptyl sulfone

Step a:

Dissolve 2-chloroethyl heptyl sulfide (1.0 g, 5.13 mmol) in methylene chloride (50 mL). Add meta-chloroperbenzoic acid (3.2 g, 15 mmol) portionwise and stir at room temperature for 1 hour. Add addition meta-chloroperbenzoic acid (1.0 g) and stir at room temperature for 2 hours. Treat with saturated sodium meta bisulfite (until negative starch-iodide test) and basify with saturated sodium hydrogen carbonate. Extract with methylene chloride (2×25 mL), dry ($MgSO_4$) and evaporate in vacuo to yield 1.23 g 2-chloroethyl heptyl sulfone as a white solid; MS ($CI/CH_4$) m/z 227(M+1).

Step b:

Mix 2-chloroethyl heptyl sulfone (1.1 g, 5 mmol) and piperidine (10 mL). Stir at 60° C. overnight. Add addition piperidine (5 mL) and stir at 60° C. overnight. Cool to room temperature, partition between 5N sodium hydroxide and ethyl ether. Separate the organic phase and extract the aqueous phase with ethyl ether (2×25 mL). Combine the organic phases, dry ($MgSO_4$) and evaporate in vacuo to yield 1.2 g orange oil which crystallizes. Purify by silica gel chromatography (ethyl acetate) to yield 930 mg. Purify again by silica gel chromatography (hexane, then 10% ethyl acetate/hexane, then 50% ethyl acetate/hexane) to yield 360 mg of the title compound as a yellow oil.

Anal. Calcd for $C_{14}H_{29}NO_2S$: C, 61.05; H, 10.61; N, 5.08; Found: C, 61.29; H, 10.55; N, 4.79.

EXAMPLE 14

5-[1-(4-Hydroxy)piperidyl]pentyl isopentyl Sulfoxide

Step b:

Heat 5-chloropentyl isopentyl sulfoxide (760 mg, 3.38 mmoL) and 4-hydroxypiperidine (2 g) at 125° C. for 1 hour. Partition between 5N sodium hydroxide and ethyl ether. Separate the organic phase and extract the aqueous phase with ethyl ether (2×25 mL). Combine the organic phases and dry ($MgSO_4$). Evaporate the solvent in vacuo and purify by silica gel chromatography to give the title compound.

EXAMPLE 15

5-[1-(4-Hydroxy)piperidyl]pentyl isopentyl sulfone

Step b:

Heat 5-chloropentyl isopentyl sulfone (770 mg, 3.2 mmoL) and 4-hydroxypiperidine (2 g) at 125° C. for 1 hour. Partition between 5N sodium hydroxide and ethyl ether. Separate the organic phase and extract the aqueous phase with ethyl ether (2×25 mL). Combine the organic phases and dry ($MgSO_4$). Evaporate the solvent in vacuo and purify by silica gel chromatography to give the title compound.

The following compounds can be prepared by procedures analogous to those described above in Examples 6–15:

5-[1-(3-hydroxy)piperidyl]pentyl isopentyl sulfoxide
5-[1-(3-hydroxy)piperidyl]pentyl isopentyl sulfone
5-[1-(4-hydroxy-3,3-dimethyl)piperidyl]pentyl isopenyl sulfoxide
5-[1-(4-hydroxy-3,3-dimethyl)piperidyl]pentyl isopenyl sulfone
5-[1-(3,4-dihydroxy)piperidyl]pentyl isopentyl sulfoxide
5-[1-(3,4-dihydroxy)piperidylid]pentyl isopentyl sulfone
3-[1-(3-hydroxy)piperidyl]propyl isopentyl sulfoxide
3-[1-(4-hydroxy-3,3-dimethyl)piperidyl]propyl isopentyl sulfoxide
3-[1-(4-hydroxy-3,3-dimethyl)piperidyl]propyl isopentyl sulfone
3-[1-(3-hydroxy)piperidyl]propyl isopentyl sulfone
3-[1-(3,4-dihydroxy)piperidyl]propyl isopentyl sulfoxide
3-[1-(3,4-dihydroxy)piperidyl]propyl isopentyl sulfone
4-(1-piperidyl) butyl ethyl sulfoxide
4-(1-piperidyl) butyl ethyl sulfone
2-(1-piperidyl) ethyl butyl sulfoxide
2-(1-piperidyl) ethyl butyl sulfone
2-(1-piperidyl) ethyl pentyl sulfoxide
2-(1-piperidyl) ethyl pentyl sulfone
2-(1-piperidyl) ethyl hexyl sulfoxide
2-(1-piperidyl) ethyl hexyl sulfone
4-[1-(4-methyl)piperidyl]butyl ethyl sulfoxide
4-[1-(4-methyl)piperidyl]butyl ethyl sulfone
2-[1-(3-methyl)piperidyl]ethyl butyl sulfoxide
2-[1-(3-methyl)piperidyl]ethyl butyl sulfone
2-[1-(3,4-dimethyl)piperidyl]ethyl pentyl sulfoxide
2-[1-(3,4-dimethyl)piperidyl]ethyl pentyl sulfone
9-(1-piperidyl)nonanyl isopropyl ether
9-[1-(4-hydroxy)piperidyl]nonanyl isopropyl ether
9-[1-(3,4-dihydroxy)piperidyl]nonanyl isopropyl ether
9-[1-(3-hydroxy)piperidyl]nonanyl isopropyl ether
3-(1-piperidyl)propyl isopropyl ether
4-(1-piperidyl)butyl isopropyl ether.

The compounds of formula (1) wherein R is a group represented by formula (2) can be prepared by techniques and procedures well known and appreciated by one of ordinary skill in the art. A general synthetic scheme for preparing these compounds is set forth in Scheme C, wherein all substituents, unless otherwise indicated, are as previously defined.

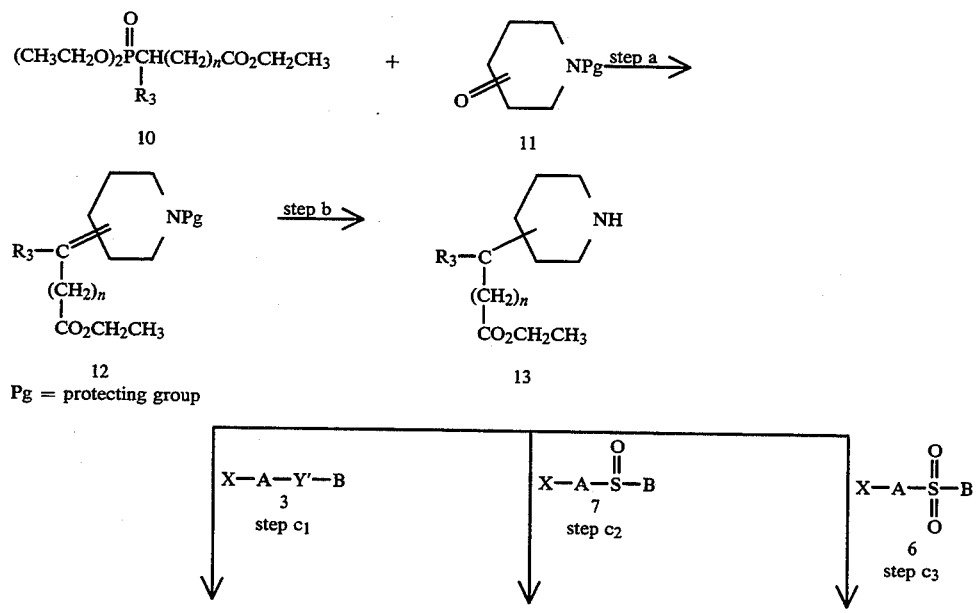

Scheme C

Pg = protecting group

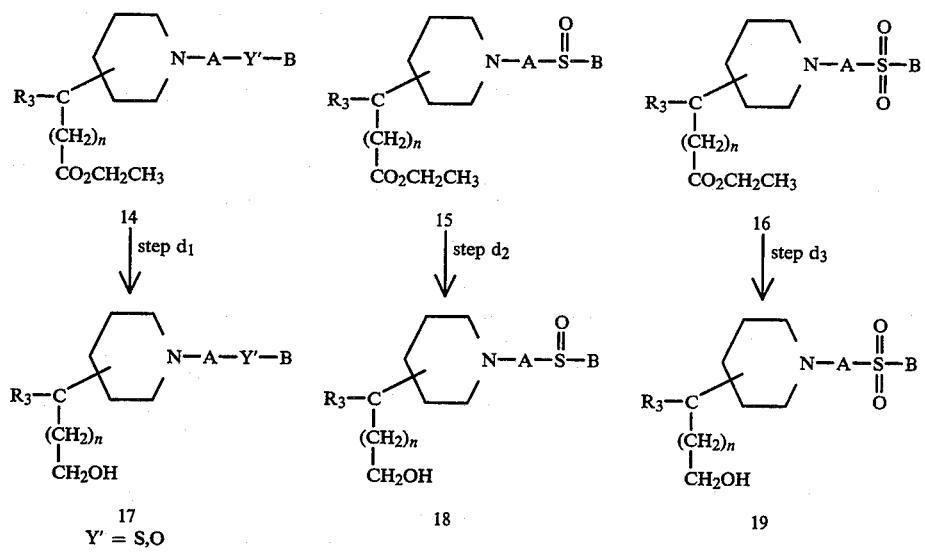

Scheme C provides a general synthetic scheme for preparing compounds of formula (1) wherein R is a group represented by formula (2). In general, compounds of formula (1) wherein R is a group represented by formula (2) can be prepared in a four-step process.

In step a, a Wittig type reaction is performed in which an appropriate alkyl phosphonate compound of structure 10, wherein n is zero or an integer from 1 to 3 and $R_3$ is ($C_1$–$C_4$) alkyl, is reacted with a 3- or 4-piperidinone compound of structure 11 to form intermediate substituted piperidinylidene compound of structure 12. For example, the alkyl phosphonate compound of structure 10 is first reacted with a non-nucleophilic base, such a n-butyllithium, in a suitable aprotic solvent, such as tetrahydrofuran, to form the corresponding lithium salt. The lithium salt is then reacted with the appropriate piperidinone compound of structure 11 to give the appropriate substituted piperidinylidene compound of structure 12.

In step b, the olefin functionality of the appropriate substituted piperidinylidene compound of structure 12 can be reduced by techniques and procedures well known and appreciated in the art to give substituted piperidine compounds of structure 13. In certain cases, for example when Pg is benzyl, the protecting group is cleaved from the nitrogen of the piperidine ring in the same step. For example, the olefin functionality of the appropriate substituted piperidinylidene compound of structure 12 can be reduced by means of hydrogenation under pressure of hydrogen gas in the presence of a catalytic amount of a suitable hydrogenation catalyst, such as 10% palladium (Pd/C), in a suitable acidic medium, such as acetic acid.

In step c1, the appropriate substituted piperidine compound of structure 13 can be reacted with the appropriate haloalkylene alkyl sulfide compound or the appropriate haloalkylene alkyl ether compound of structure 3 to give the corresponding N-alkylated alkyl sulfide compound or N-alkylated alkyl ether compound of structure 14 as described previously in Scheme A, step b.

In step c2, the appropriate substituted piperidine compound of structure 13 can be reacted with the appropriate haloalkylene alkyl sulfoxide compound of structure 7 to give the corresponding N-alkylated alkyl sulfoxide compound of structure 15 as described previously in Scheme A, step b.

In step c3, the appropriate substituted piperidine compound of structure 13 can be reacted with the appropriate haloalkylene alkyl sulfone compound of structure 6 to give the corresponding N-alkylated alkyl sulfone compound of structure 16 as described previously in Scheme A, step b.

In step d1, the carboethoxy functionality of the appropriate N-aklylated alkyl sulfide compound or the appropriate N-alkylated alkyl ether compound of structure 13. can be reduced to the corresponding hydroxymethylene by techniques and procedures well known and appreciated by one of ordinary skill in the art. For example, the carboethoxy functionality of the appropriate N-alkylated alkyl sulfide compound or the appropriate N-alkylated alkyl ether compound of structure 14 can be reduced with diisobutylaluminum hydride (DIB-AL-H) in a suitable aprotic solvent, such as tetrahydrofuran, to give the substituted piperidine compound of structure 17.

In step d2, the carboethoxy functionality of the appropriate N-aklylated alkyl sulfoxide compound of structure 15 can be reduced to the corresponding hydroxymethylene as described above in step d1 to give the substituted piperidine compound of structure 18.

In step d3, the carboethoxy functionality of the appropriate N-aklylated alkyl sulfone compound of structure 16 can be reduced to the corresponding hydroxymethylene as described above in step d1 to give the substituted piperidine compound of structure 19.

Starting materials for use in the general synthetic procedures outlined in Scheme C are readily available to one of ordinary skill in the art.

The piperidinone 11 has a protecting group (Pg) at the nitrogen position. Appropriate protecting groups are well known in the art and include benzyl, benzyloxy, p-methoxybenzyl, as well as other protecting groups, which should not be construed as limiting. The alkyl phosphonate 10 is chosen such that $R_3$ and n have the same definitions as that desired in the final product. It will be understood that while the alkyl phosphonate represented by structure 10 is a triethyl ester, other alkyl esters such as the methyl, propyl or isopropyl esters, for example, may also be utilized and this should not be construed as limiting.

The following examples represent typical syntheses as described in Schemes C. These examples are understood to be illustrative only and are not intended to limit the scope of the present invention in any way.

EXAMPLE 16

2-[1-(5-Pentylene isopentyl sulfide)-4-piperidyl]propanol

Step a:

Dissolve triethyl 2-phosphonopropionate (5.72 g, 24 mmol) in anydrous tetrahydrofuran (250 mL), cool to −78° C. and place under argon atomsphere. Add a solution of n-butyllithium in hexane (16.3 mL, 26 mmol). Stir at −78° C. for 10 minutes, then add, by dropwise addition, a solution of N-benzyl-4-piperidinone (3.79 g, 20 mmol) in tetrahydrofuran (50 mL). Stir for 10 minutes, allow to warm to room temperature, and stir for an additional 17 hours. Dilute with saturated ammonium chloride (100 mL), wash twice with 10% sodium hydroxide and dry ($MgSO_4$). Evaporate the solvent in vacuo to yield 6.58 g. Purify by silica gel chromatography (25% ethyl acetate/hexane) to yield 5.25 g (96%) of 2-[1-(phenylmethyl)-4-piperidylinylidene]propanoic acid, ethyl ester as a colorless oil; MS ($CI/CH_4$) m/z 274 (M+1), 228(M+1-EtOH), 196(M+H-$C_6H_6$).

Step b:

Dissolve 2-[1-(phenylmethyl)-4-piperidinylidene]-propanoic acid, ethyl ester (1.5 g, 5.5 mmol) in acetic acid (50 mL).and place in a Paar hydrogenation flask. Add 10% palladium(C) (500 mg). Charge the vessel to 50 psi and shake for 18 hours. Filter the solution through Celite and remove the solvent in vacuo to give 2-(4-piperidyl)propanoic acid, ethyl ester.

Step $c_1$:

Mix 2-(4-piperidyl)propanoic acid, ethyl ester (1.85 g, 10 mmol), chloropentyl isopentyl sulfide (2.09 g, 10 mmol) and pyridine (25 mL). Heat at reflux for 15 hours. Cool to room temperature and dilute with ethyl ether. Separate the organic phase, wash with 10% sodium hydroxide, then water and dry ($MgSO_4$). Evaporate the solvent in vacuo and purify by silica gel chromatography to give 2-[1-(5-pentylene isopentyl sulfide)-4-piperidyl]propanoic acid, ethyl ester.

Step $d_1$:

Dissolve 2-[1-(5-pentylene isopentyl sulfide)-4-piperidyl]propanoic acid, ethyl ester (701 mg, 1.96 mmol) in anhydrous tetrahydrofuran (25 mL). Add diisobutylaluminun hydride (DIBAL-H) (4.2 mL of a 1M solution in hexane, 4.2 mmol). Stir at room temperature for 16 hours and quench with methanol. Dilute with ethyl ether, filter and evaporate the solvent in vacuo to yield 606 mg of the title compound. Purify by silica gel chromatography.

EXAMPLE 17

2-[1-(5-Pentylene isopentyl sulfoxide)-4-piperidyl]propanol

Step $c_2$:

Mix 2-(4-piperidyl)propanoic acid, ethyl ester (1.85 g, 10 mmol), 5-chloropentyl isopentyl sulfoxide (2.25 g, 10 mmol) and pyridine (25 mL). Heat at 86° C. for 15 hours. Cool to room temperature and dilute with ethyl ether. Separate the organic phase, wash with 10% sodium hydroxide, then water and dry ($MgSO_4$). Evaporate the solvent in vacuo and purify by silica gel chromatography to give 2-[1-(5-pentylene isopentyl sulfoxide)-4-piperidyl]propanoic acid, ethyl ester.

Step $d_2$:

Dissolve 2-[1-(5-pentylene isopentyl sulfoxide)-4-piperidyl]propanoic acid, ethyl ester (732 mg, 1.96 mmol) in anhydrous tetrahydrofuran (25 mL). Add DIBAL-H (4.2 mL of a 1M solution in hexane, 4.2 mmol). Stir at room temperature and quench with methanol. Dilute with ethyl ether, filter and evaporate the solvent in vacuo and purify by silica gel chromatography to give the title compound.

EXAMPLE 18

2-[1-(5-Pentylene isopentyl sulfone)-4-piperidyl]proponal

Step $c_3$:

Mix 2-(4-piperidyl)propanoic acid, ethyl ester (1.85 g, 10 mmol), 5-chloropentyl isopentyl sulfone (2.41 g, 10 mmol) and pyridine (25 mL). Heat at 86° C. for 15 hours. Cool to room temperature and dilute with ethyl ether. Separate the organic phase, wash with 10% sodium hydroxide, then water and dry ($MgSO_4$). Evaporate the solvent in vacuo and purify by silica gel chromatography to give 2-[1-(5-pentylene isopentyl sulfone)-4-piperidyl]propanoic acid, ethyl ester.

Step $d_3$:

Dissolve 2-[1-(5-pentylene isopentyl sulfone)-4-piperidyl]propanoic acid, ethyl ester (764 mg, 1.96 mmol) in anhydrous tetrahydrofuran (25 mL). Add DIBAL-H (4.2 mL of a 1M solution in hexane, 4.2 mmol). Stir at room temperature for 1 6 hours and quench with methanol. Dilute with ethyl ether, filter and evaporate the solvent in vacuo and purify by silica gel chromatography to yield the title compound.

The following compounds can be prepared by procedures analogous to those described above in Examples 16–18:

2-[1-(3-propylene isopentyl sulfone)-4-(3-hydroxy)-piperidyl]propanol

2-[1-(4-butylene isopentyl sulfone)-4-(3-hydroxy)-piperidyl]propanol

2-[1-(3-propylene isopentyl sulfone)-4-(2,3-dimethyl)-piperidyl]propanol

2-[1-(4-butylene isopentyl sulfone) -4-(2,3-dimethyl)-piperidyl]propanol

2-[1-(3-propylene isopentyl sulfoxide)-4-(3-hydroxy)-piperidyl]propanol

2-[1-(4-butylene isopentyl sulfoxide)-4-(3-hydroxy)-piperidyl]propanol

2-[1-(3-propylene isopentyl sulfoxide) -4-(2,3-dimethyl)-piperidyl]propanol

2-[1-(4-butylene isopentyl sulfoxide) -4-(2,3-dimethyl)-piperidyl]propanol

2-[1-(3-propylene isopentyl sulfide)-4-(3-hydroxy)-piperidyl]propanol

2-[1-(4-butylene isopentyl sulfide) -4-(3-hydroxy)-piperidyl]propanol

2-[1-(3-propylene isopentyl sulfide) -4-(2,3-dimethyl)-piperidyl]propanol

2-[1-(4-butylene isopentyl sulfide) -4-(2,3-dimethyl)-piperidyl]propanol.

Alternatively, compounds of formula (1) can be prepared according to the procedure set forth in Scheme D wherein all substituents, unless otherwise indicated, are previously defined.

Scheme D

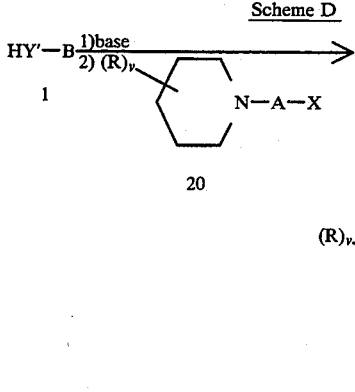

Y' = S, O

Scheme D provides an alternate general synthetic scheme for preparing compounds of formula (1) wherein Y is oxygen or sulfur. In general, an appropriate N-alkylene alkyl sufide or N-alkylene alkyl ether compound of structure 5 can be prepared by a Williamson type reaction. For example, an appropriate thiol compound of structure 1 can be converted to the corresponding sodium salt by reaction with sodium ethoxide in a suitable solvent, such as ethanol. An appropriate alcohol compound of structure 1 can be converted to the corresponding sodium salt by reaction with sodium hydride in a suitable solvent, such as excess alcohol compound of structure 1. The appropriate sodium thioalkoxide or sodium alkoxide is then reacted with the appropriate N-haloalkylene piperidine compound of structure 20 in a suitable protic solvent, as described above, to give the appropriate N-alkylated alkyl sulfide compound or the appropriate N-alkylated alkyl ether compound of structure 5.

Starting materials for use in the general synthetic procedure outlined on Scheme D are readily available to one of ordinary skill in the art.

The following examples present typical syntheses as described in Scheme D. These examples are understood to be illustrative only and are not intended to limit the scope of the present invention in any way.

EXAMPLE 19

2-(1-Piperidyl)ethyl heptyl ether, hydrochloride salt

Step a:

Mix sodium hydride (2.2 g of 60%, 54.3 mmol) and anhydrous tetrahydrofuran (50 mL) under nitrogen atmosphere. Add by dropwise addition, a solution of n-heptanol (6.3 g, 54.3 mmol) in anhydrous tetrahydrofuran (10 mL) and stir overnight. Add, by dropwise addition, the above solution of sodium heptoxide to a mixture of N-(2-chloroethyl)piperidine hydrochloride (5.0 g, 27.2 mmol) in anhydrous tetrahydrofuran (25 mL). Heat at reflux for 72 hours. Add additional sodium heptoxide (1 mL n-heptanol and 0.5 g sodium) and continue at reflux overnight. Cool to room temperature, filter and concentrate in vacuo. Partition the residue between 2N HCl and ethyl ether. Separate the organic phase and wash the aqueous phase with ethyl ether (2×100 mL). Basify the aqueous phase to pH 11 with 5N NaOH and extract the product with ethyl ether (3×75 mL). Dry (MgSO4) and evaporate in vacuo to yield 5.35 g (84%) yellow oil. Dissolve the oil in ethyl ether and treat with anhydrous hydrochloric acid. Collect the resulting white solid by vacuum filtration and recrystallize (ethyl acetate) twice to yield 1.78 g waxy solid; mp 100°-102° C. Recrystallize again (ethyl acetate/hexane) to yield 1.1 g of the title compound as a waxy off-white solid; mp 110°-11° C.

Anal. Calcd for $C_{14}H_{29}NO \cdot HCl$: C, 63.78; H, 11.46; N, 5.31; Found: C, 62.98; H, 11.70; N, 5.30.(TG % loss=3.2%)

EXAMPLE 20

3-(1-Piperidyl)propyl hexyl ether, hydrochloride salt

Step a:

Mix sodium hydride (2.04 g of 60%, 51 mmol) and anhydrous tetrahydrofuran (50 mL) under nitrogen atmosphere. Add by dropwise addition, a solution of n-hexanol (6.4 mL, 51 mmol) in anhydrous tetrahydrofuran (10 mL) and stir for 4 hours. Add, portionwise, N-(gamma-chloropropyl)piperidine hydrochloride (5.0 g, 25.2 mmol) (extreme foaming). Heat at reflux for 72 hours. Add additional sodium hexoxide (1 mL n-hexanol and 0.5 g sodium) and continue at reflux overnight. Cool to room temperature, filter and concentrate in vacuo. Partition the residue between 2N HCl and ethyl ether. Separate the organic phase and wash the aqueous phase with ethyl ether (2×100 mL). Basify the aqueous phase to pH 11 with 5N NaOH and extract the product with ethyl ether (3×75 mL). Dry (MgSO4) and evaporate in vacuo to yield 2.2 g (84%) clear oil. Dissolve the oil in ethyl ether and treat with anhydrous hydrochloric acid. Collect the resulting white solid by vacuum filtration and recrystallize (ethyl acetate) to yield 1.8 g of the title compound as a white solid; mp 145°-146° C.

Anal. Calcd for $C_{14}H_{29}NO \cdot \frac{1}{4}H_2O \cdot HCl$: C, 62.66; H, 11.46; N, 5.22; Found: C, 62.66; H, 11.54; N, 5.30.(TG % loss=1.7%)

EXAMPLE 21

2-(1-Piperidyl)ethyl heptyl sulfide, hydrochloride salt

Step a:

Generate sodium ethoxide by carefully adding sodium metal (1.4 g, 60 mmol) to absolute ethanol (50 mL). Add ½ of the sodium ethoxide (30 mL) to a solution of N-(2-chloroethyl)-piperidine hydrochloride (5.0 g, 27.2 mmol) in absolute ethanol. Add the other ½ of the sodium ethoxide (30 mL) to a solution of heptyl mercaptan (4.6 mL, 30 mmol) in absolute ethanol. Mix the two and stir at room temperature overnight. Concentrate in vacuo, partition between water and ethyl acetate and separate the organic phase. Extract the aqueous phase with ethyl acetate (2×50 mL), combine the organic phases and dry (MgSO4). Evaporate the solvent in vacuo to yield 6.34 g yellow oil. Dissolve the oil in ethyl ether, filter and treat with anhydrous hydrochloric acid. Collect the resulting white solid by vacuum filtration (5.6 g) and recrystallize (ethyl acetate/isopropanol) to yield 3.12 g of the title compound as white crystals; mp 169°-70° C.

Anal. Calcd for $C_{14}H_{29}NS \cdot HCl$: C, 60.07; H, 10.80; N, 5.00; Found: C, 59.76; H, 11.16; N, 5.04.

The following example illutstrates the utility of compounds of formula (1) in inhibiting cholesterol biosynthesis. This example is understood to be illustrative only and is not intended to limit the scope of the present invention in any way. Microsomes, prepared by ultracentrifugation of homogenates of rat liver, are incubated at 37° C. for 45 muinutes in the presence of 60 μM $^3$H-squalene, 2.0 mM NADPH, 0.01 mM FAD, and the high speed supernatant fraction from the microsomal preparation. Blanks, in which NADPH has been omitted, are run simultaneously with the test compounds. Compounds are tested at concentrations of 0.0 to 100.0 μM.

EXAMPLE 22
Inhibition of Cholesterol Biosynthesis a) TLC Assay:

Following incubation, the samples are saponified, standards are added to each sample, and then the reaction products are extracted into hexane. The hexane extracts are dried and then the dried extracts are redissolved in chloroform. The reaction products (3S)-2,3-oxidosqualene and lanosterol contained in the extracts are then separated by TLC. Spots containing the reaction products are scraped from the TLC plates and counted for $^3$H-radioactivity in a scintillation counter. An $IC_{50}$ for squalene epoxidase and oxidosqualene cyclase is calculated.

b) HPLC Assay:

Following incubation, reactions are stopped by the addition of chloroform:methanol, standards are added, then reaction products and standards are extracted into chloroform. The chloroform extracts are dried, and the residue is dissolved in toluene:methanol. The reaction products and standards contained in the dissolved residue are separated by high performance liquid chromatography (HPLC). Chromatographic peaks containing reaction products are monitored for $^3$H- radioactivity with a flow-through scintillation counter connected in series with the HPLC column. An $IC_{50}$ is calculated for squalene epoxidase and oxidosqualene cyclase based on the radioactivity in controls and samples.

Table 1 provides a summary of the testing data for the inhibition of oxidosqualene cyclase by compounds of formula (1).

| Compound | Cyclase, $IC_{50}$ |
|---|---|
| A | 24 μM |
| B | 13 μM |
| C | 5 μM |
| D | 48 μM |
| E | >100 μM |

Compound A: 5-(1-piperidyl)pentyl isopentyl sulfide
Compound B: 5-(1-piperidyl)pentyl isopentyl sulfoxide
Compound C: 5-(1-piperidyl)pentyl isopentyl sulfone
Compound D: 5-(1-piperidyl)propyl isopentyl sulfide
Compound E: 5-(1-piperidyl)ethyl ethyl sulfide In a further embodiment, the present invention provides a method of inhibiting cholesterol biosynthesis in a patient in need thereof comprising administering to said patient an effective cholesterol biosynthesis inhibitory amount of a compound of formula (1). The present invention also provides a method of lowering plasma cholesterol in a patient in need thereof, and a method of treating a patient afflicted with hypercholesterolemia, comprising administering to said patient an effective hypocholesterolemic amount of a compound of formula (1).

It is believed that the compounds of the present invention exert their inhibitory effect on cholesterol biosynthesis through inhibition of squalene epoxidase and/or oxidosqualene cyclase. However, the present invention is not intended to be limited to a particular mechanism of action in achieving inhibition of cholesterol biosynthesis in a patient in need thereof.

As used herein, the term "patient" refers to warm-blooded animals or mammals, including humans. A patient is in need of treatment to inhibit cholesterol biosynthesis or to reduce plasma cholesterol when the patient is suffering from hypercholesterolemia, such as, for example, in the case of a patient suffering from familial hyperlipidemia.

Hypercholesterolemia is a disease state characterized by levels of plasma cholesterol or of LDL cholesterol which are elevated by a clinically significant amount over that considered normal by those of ordinary skill in the art. The identification of those patients who are in need of treatment for hypercholesterolemia is well within the ability and knowledge of one skilled in the art. For example, individuals who have serum cholesterol levels or LDL cholesterol levels, as determined by clinical laboratory tests, which are substantially and chronically elevated over that considered normal by those of ordinary skill in the art, are patients in need of treatment for hypercholesterolemia. By way of further example, individuals who are at risk of developing hypercholesterolemia can also be patients in need of treatment for hypercholesterolemia. A clinician skilled in the art can readily identify, by the use of clinical tests, physical examination and medical/family history, those patients who are suffering from hypercholesterolemia and those who are at risk of developing hypercholesterolemia and thus readily determine if an individual is a patient in need of treatment for hypercholesterolemia.

An effective hypocholesterolemic amount of a compound of formula (1) is an amount which is effective in reducing plasma cholesterol levels or LDL cholesterol levels in a patient in need thereof. As such, successful treatment of a patient for hypercholesterolemia is understood to include reducing a patient's plasma cholesterol or LDL cholesterol levels. Successful treatment for hypercholesterolemia is also understood to include prophylaxis in preventing clinically significant elevations in plasma cholesterol or in LDL cholesterol levels in a patient who is at risk of the development of hypercholesterolemia.

An effective cholesterol biosynthesis inhibitory amount of a compound of formula (1) is an amount which is effective in inhibiting cholesterol biosynthesis in a patient in need thereof which results in the lowering of plasma cholesterol levels or LDL cholesterol levels.

An effective hypocholesterolemic dose or an effective cholesterol biosynthesis inhibitory dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective hypocholesterolemic amount, and an effective cholesterol biosynthesis inhibitory amount, of a compound of formula (1) will generally vary from about 0.1 milligram per kilogram of body weight per day (mg/kg/day) to about 500 mg/kg/day. A daily dose of from about 0.3 mg/kg to about 80 mg/kg is preferred.

In addition, the present invention provides a method of treating a patient afflicted with a fungal infection comprising administering to said patient an effective antifungal amount of a compound of formula (1). Certain fungi are dependent on the biosynthesis of endogenous ergosterol for their growth and reproduction as described in "Sterol Biosynthesis Inhibitors; Pharmaceutical and Agrochemical Aspects" Edited by D. Berg and M. Plempel (Ellis Horwood, 1988). By inhibiting the biosynthesis of ergosterol, the compounds of formula (1) inhibit the growth and reproduction of fungi and thus provide an antifungal effect.

As used herein, the term "fungal infection" refers to an invasion and multiplication of fungi into the tissues of a patient. Fungal infections for which treatment with a compound of formula (1) will be particularly useful for include infections of: *Microsporum canis, Ctenomyces mentagrophytes, Trichophyton rubrum, Phialophora verrucosa, Cryptococcus neoformans, Candida tropicalis, Candida albicans,* Mucor species, *Aspergillus fumigatus, Sporotrichum schenckii* and Saprolegnia species.

An effective antifungal amount of a compound of formula (1) refers to an amount which is effective, upon single or multiple administration to the patient, in controlling the growth of the fungus. As used herein, "controlling the growth" of the fungus refers to slowing, interrupting, arresting or stopping its growth or its reproduction, and does not necessarily indicate a total elimination of the fungus.

An effective antifungal dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective antifungal amount of a compound of formula (1) will generally vary from about 0.1 milligram per kilogram of body weight per day (mg/kg/day) to about 500 mg/kg/day. Where systemic administration is desired, a daily dose of from about 0.3 mg/kg to about 80 mg/kg is preferred. Where topical administration is desired, a daily dose of from about 5 to about 500 mg and more particularly from about 20 to about 80 mg of the active ingredient is preferred.

In effecting treatment of a patient, compounds of formula (1) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances.

Compounds of formula (1) can be administered in the form of pharmaceutical compositions or medicaments which are made by combining the compounds of formula (1) with pharmaceutically acceptable carriers or excipients, the proportion and nature of which are determined by the chosen route of administration, and standard pharmaceutical practice.

In another embodiment, the present invention provides compositions comprising a compound of formula (1) in admixture or otherwise in association with one or more inert carriers. These compositions are useful, for example, as assay standards, as convenient means of making bulk shipments, or as pharmaceutical compositions. An assayable amount of a compound of formula (1) is an amount which is readily measurable by standard assay procedures and techniques as are well known and appreciated by those skilled in the art. Assayable amounts of a compound of formula (1) will generally vary from about 0.001% to about 75% of the composition by weight. Inert carriers can be any material which does not degrade or otherwise covalently react with a compound of formula (1). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective amount of a compound of formula (1) in admixture or otherwise in association with one or more pharmaceutically acceptable carriers or excipients.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, the compounds of formula (1) may be incorporated with excipients and used in the form of tablets, troches, capsules, elixirs, suspensions, syrups, wafers, chewing gums and the like. These preparations should contain at least 4% of the compound of formula (1), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, the compounds of formula (1) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of formula (1) in their end-use application.

The compounds of formula (1) wherein Y is sulfone are generally preferred. Compounds of formula (1) wherein A is pentyl are preferred. Compounds of formula (1) wherein B is isopentyl are preferred. Compounds of formula (1) wherein the piperidyl moiety is 1-piperidyl are generally preferred.

The following specific compounds of formula (1) are particularly preferred in the end-use application of the compounds of the present invention:
5-(1-piperidyl)pentyl isopentyl sulfide
5-(1-piperidyl)pentyl isopentyl sulfoxide
5-(1-piperidyl)pentyl isopentyl sulfone
3-(1-piperidyl)propyl isopentyl sulfide
2-(1-piperidyl)ethyl ethyl sulfide.

What is claimed is:

1. A method of inhibiting the biosynthesis of cholesterol in a patient in need thereof comprising administering to said patient an effective cholesterol biosynthesis inhibiting amount of a compound of the formula

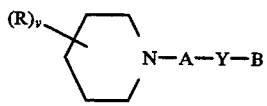

wherein
Y is oxygen, sulfur, sulfinyl or sulfonyl;
A is a $C_2$-$C_{15}$ alkylene having 0 to 3 double bonds;
B is a $C_2$-$C_{15}$ alkyl having 0 to 3 double bonds;
v is a integer 0, 1 or 2; and
R is hydroxy, $C_1$-$C_4$ alkyl or a radical of the formula

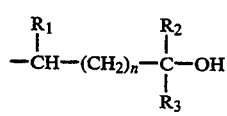

wherein
n is an integer 0, 1, 2 or 3; and
$R_1$, $R_2$ and $R_3$ are each independently hydrogen or a $C_1$-$C_4$ alkyl.

2. A method of lowering plasma cholesterol in a patient in need thereof comprising administering to said patient an effective hypocholesterolemic amount of a compound of the formula

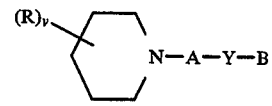

wherein
Y is oxygen, sulfur, sulfinyl or sulfonyl;
A is a $C_2$-$C_{15}$ alkylene having 0 to 3 double bonds;
B is a $C_2$-$C_{15}$ alkyl having 0 to 3 double bonds;
v is an integer 0, 1 or 2; and
R is hydroxy, $C_1$-$C_4$ alkyl or a radical of the formula

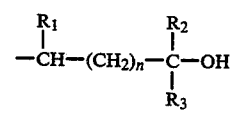

wherein
n is an integer 0, 1, 2 or 3; and
$R_1$, $R_2$ and $R_3$ are each independently hydrogen or a $C_1$-$C_4$ alkyl.

3. A method of treating a patient afflicted with hypercholesterolemia comprising administering to said patient an effective hypocholesterolemic amount of a compound of the formula

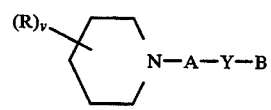

wherein
Y is oxygen, sulfur, sulfinyl or sulfonyl;
A is a $C_2$-$C_{15}$ alkylene having 0 to 3 double bonds;
B is a $C_2$-$C_{15}$ alkyl having 0 to 3 double bonds;
v is an integer 0, 1 or 2; and
R is hydroxy, $C_1$-$C_4$ alkyl or a radical of the formula

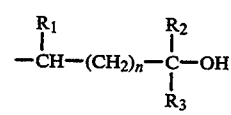

wherein
n is an integer 0, 1, 2 or 3; and
$R_1$, $R_2$ and $R_3$ are each independently hydrogen or a $C_1$-$C_4$ alkyl.

4. A pharmaceutical composition comprising an effective hypocholesterolemic amount of a compound of the formula

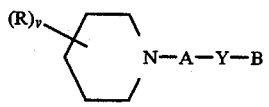

wherein

Y is oxygen, sulfur, sulfinyl or sulfonyl;

A is a $C_2$-$C_{15}$ alkylene having 0 to 3 double bonds;

B is a $C_2$-$C_{15}$ alkyl having 0 to 3 double bonds;

v is an integer 0, 1 or 2; and

R is hydroxy, $C_1$-$C_4$ alkyl or a radical of the formula

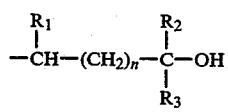

wherein n is an integer 0, 1, 2 or 3; and $R_1$, $R_2$ and $R_3$ are each independently hydrogen or a $C_1$-$C_4$ alkyl in admixture or otherwise in association with one or more pharmaceutically acceptable carriers or excipients.

5. A method of claim 1 wherein the compound is [2-(1-piperidyl)pentyl isopentyl sulfide]5-(1-piperidyl)pentyl isopentyl sulfide.

6. A method of claim 1 wherein the compound is [2-(1-piperidyl)pentyl isopentyl sulfoxide]5-(1-piperidyl)pentyl isopentyl sulfoxide.

7. A method of claim 1 wherein the compound is [2-(1-piperidyl)pentyl isopentyl sulfone]5-(1-piperidyl)pentyl isopentyl sulfone.

8. A method of claim 1 wherein the compound is [2-(1-piperidyl)propyl isopentyl sulfide]3-(1-piperidyl)propyl isopentyl sulfide.

9. A method of claim 1 wherein the compound is 2-(1-piperidyl)ethyl ethyl sulfide.

10. A method of treating a patient afflicted with a fungal infection comprising administering an effective antifungal amount of a compound of the formula

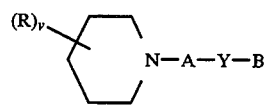

wherein

Y is oxygen, sulfur, sulfinyl or sulfonyl;

A is a $C_2$-$C_{15}$ alkylene having 0 to 3 double bonds;

B is a $C_2$-$C_{15}$ alkyl having 0 to 3 double bonds;

v is an integer 0, 1 or 2; and

R is hydroxy, $C_1$-$C_4$ alkyl or a radical of the formula

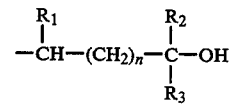

wherein n is an integer 0, 1, 2 or 3; and $R_1$, $R_2$ and $R_3$ are each independently hydrogen or a $C_1$-$C_4$ alkyl.

11. A method of claim 1 wherein the compound is 9-(1-piperidyl)nonanyl isopropyl ether.

12. A method of claim 1 wherein the compound is 3-(1-piperidyl)propyl hexyl ether.

13. A method of claim 1 wherein the compound is 2-(1-piperidyl)ethyl heptyl ether.

* * * * *

UNITED STATES PATENT AND TRADEMARK OFFICE
CERTIFICATE OF CORRECTION

PATENT NO. : 5,348,964                                Page 1 of 2

DATED : Sep. 20, 1994

INVENTOR(S) : Charlotte L. Barney, James R. McCarthy & Marion W. Wannamaker

It is certified that error appears in the above-identified patent and that said Letters Patent is hereby corrected as shown below:

Column 1, Line 25 patent reads: "2,3oxidosqualene" and should read -- 2,3-oxidosqualene --.

Column 2, Line 22 patent reads: "uerrucosa," and should read -- verrucosa, --.

Column 6, Line 10 patent reads: "1,9dibromononane" and should read -- 1,9-dibromononane --.

Column 10, Line 41 patent reads: "$Cl_3$ and should read -- $C_{13}$ --.

Column 11, Line 51 patent reads: "2chloroethyl" and should read -- 2-chloroethyl --.

Column 11, Line 66 patent reads: "ethyl heptyl" and should read -- ethyl heptyl sulfoxide --.

Column 12, Line 29 patent reads: "2chloroethyl" and should read -- 2-chloroethyl --.

Column 16, Line 37 patent reads: "structure 13" and should read -- structure 14 --.

Column 17, Line 52 patent reads: "diisobutylauminun" and should read -- diisobutylalyminum --.

Column 18, Line 33 patent reads: " 1 6 hours" and should read -- 16 hours --.

Column 21, Line 48 patent reads: "5-(" and should read -- 2-( --.

UNITED STATES PATENT AND TRADEMARK OFFICE
CERTIFICATE OF CORRECTION

PATENT NO. : 5,348,964
DATED : September 20, 1994
INVENTOR(S) : Charlotte L. Barney, et. al.

It is certified that error appears in the above-indentified patent and that said Letters Patent is hereby corrected as shown below:

Column 25, Line 42 patent reads: "3-(" and should read --5-(--.

Signed and Sealed this

Twenty-second Day of August, 1995

Attest:

BRUCE LEHMAN

*Attesting Officer*          *Commissioner of Patents and Trademarks*